United States Patent
Euteneuer et al.

(10) Patent No.: US 7,153,320 B2
(45) Date of Patent: Dec. 26, 2006

(54) HYDRAULIC CONTROLLED RETRACTABLE TIP FILTER RETRIEVAL CATHETER

(75) Inventors: Charles L. Euteneuer, St. Michael, MN (US); Thomas E. Broome, Hopkins, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 596 days.

(21) Appl. No.: 10/017,877

(22) Filed: Dec. 13, 2001

(65) Prior Publication Data

US 2003/0114879 A1    Jun. 19, 2003

(51) Int. Cl.
*A61M 29/00* (2006.01)
(52) U.S. Cl. .................................... 606/200
(58) Field of Classification Search ............... 606/200, 606/113–114, 127, 194; 623/1.11
See application file for complete search history.

(56) References Cited

U.S. PATENT DOCUMENTS

| | | | |
|---|---|---|---|
| 3,472,230 A | 10/1969 | Fogarty | |
| 3,502,069 A | 3/1970 | Silverman | |
| 3,952,747 A | 4/1976 | Kimmell, Jr. | |
| 3,996,938 A | 12/1976 | Clark, III | |
| 4,046,150 A | 9/1977 | Schwartz et al. | |
| 4,324,262 A * | 4/1982 | Hall | 600/569 |
| 4,425,908 A | 1/1984 | Simon | |
| 4,590,938 A | 5/1986 | Segura et al. | |
| 4,619,246 A | 10/1986 | Molgaard-Nielsen et al. | |
| 4,650,466 A | 3/1987 | Luther | |
| 4,706,671 A | 11/1987 | Weinrib | |
| 4,723,549 A | 2/1988 | Wholey et al. | |
| 4,790,812 A | 12/1988 | Hawkins, Jr. et al. | |
| 4,790,813 A | 12/1988 | Kensey | |
| 4,794,928 A | 1/1989 | Kletschka | |
| 4,807,626 A | 2/1989 | McGirr | |
| 4,873,978 A | 10/1989 | Ginsburg | |
| 4,886,061 A | 12/1989 | Fischell et al. | |
| 4,921,478 A | 5/1990 | Solano et al. | |
| 4,921,484 A | 5/1990 | Hillstead | |
| 4,926,858 A | 5/1990 | Gifford, III et al. | |
| 4,969,891 A | 11/1990 | Gewertz | |
| 4,998,539 A | 3/1991 | Delsanti | |
| 5,002,560 A | 3/1991 | Machold et al. | |
| 5,011,488 A | 4/1991 | Ginsburg | |
| 5,053,008 A | 10/1991 | Bajaj | |
| 5,071,407 A | 12/1991 | Termin et al. | |
| 5,100,423 A | 3/1992 | Fearnot | |

(Continued)

FOREIGN PATENT DOCUMENTS

DE    28 21 048    7/1980

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

(Continued)

*Primary Examiner*—(Jackie) Tan-Uyeh T. Ho
(74) *Attorney, Agent, or Firm*—Crompton, Seager & Tufte LLC

(57) ABSTRACT

Distal protection filter retrieval devices and methods of retrieving a distal protection filter. A filter retrieval catheter may comprise an inner tube, an outer tube disposed over the inner tube, an annular lumen disposed between the inner tube and the outer tube, and a tapered member coupled to the lumen. The tapered member may be movable between a first position for passing a lesion and a second position retrieving a filter.

3 Claims, 4 Drawing Sheets

U.S. PATENT DOCUMENTS

| | | |
|---|---|---|
| 5,102,415 A | 4/1992 | Guenther et al. |
| 5,133,733 A | 7/1992 | Rasmussen et al. |
| 5,152,771 A | 10/1992 | Sabbaghian et al. |
| 5,152,777 A | 10/1992 | Goldberg et al. |
| 5,160,342 A | 11/1992 | Reger et al. |
| 5,224,953 A | 7/1993 | Morgentaler |
| 5,329,942 A | 7/1994 | Gunther et al. |
| 5,330,484 A | 7/1994 | Gunther et al. |
| 5,354,310 A | 10/1994 | Garnic et al. |
| 5,376,100 A | 12/1994 | Lefebvre |
| 5,421,832 A | 6/1995 | Lefebvre |
| 5,423,742 A | 6/1995 | Theron |
| 5,449,372 A | 9/1995 | Schmaltz et al. |
| 4,842,579 A | 10/1995 | Shiber |
| 5,456,667 A | 10/1995 | Ham et al. |
| 5,462,529 A | 10/1995 | Simpson et al. |
| 5,536,242 A | 7/1996 | Willard et al. |
| 5,549,626 A | 8/1996 | Miller et al. |
| 5,658,296 A | 8/1997 | Bates et al. |
| 5,662,671 A | 9/1997 | Barbut et al. |
| 5,662,703 A * | 9/1997 | Yurek et al. ............... 623/1.12 |
| 5,695,519 A | 12/1997 | Summers et al. |
| 5,720,764 A | 2/1998 | Naderlinger |
| 5,728,066 A | 3/1998 | Daneshvar |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,807,398 A | 9/1998 | Shaknovich |
| 5,810,874 A | 9/1998 | Lefebvre |
| 5,814,064 A | 9/1998 | Daniel et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,895,399 A | 4/1999 | Barbut et al. |
| 5,910,154 A | 6/1999 | Tsugita et al. |
| 5,911,734 A | 6/1999 | Tsugita et al. |
| 5,925,016 A | 7/1999 | Chornenky et al. |
| 5,925,060 A | 7/1999 | Forber |
| 5,925,062 A | 7/1999 | Purdy |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,954,745 A | 9/1999 | Gertler et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,813 A | 5/2000 | Vrba et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,336,934 B1 | 1/2002 | Gilson et al. |
| 6,344,049 B1 | 2/2002 | Levinson et al. |
| 6,346,116 B1 | 2/2002 | Brooks et al. |
| 6,371,969 B1 | 4/2002 | Tsugita et al. |
| 6,544,278 B1 * | 4/2003 | Vrba et al. ................ 606/198 |

FOREIGN PATENT DOCUMENTS

| | | |
|---|---|---|
| DE | 34 17 738 | 11/1985 |
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |

| | | |
|---|---|---|
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/04875 A1 | 2/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 98/51237 | 11/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/44428 | 8/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01/67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |

OTHER PUBLICATIONS

"Endovascular Grafts, Stents Drive Interventional Radiology Growth," *Cardiovascular Device Update*, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprosthesis: A New Technique Using Nitinol Wire," *AJR*, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," *Surgery*, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," *Cardiovascular Surgery*, 7(1):33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," *Laboratory Investigation*, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," *Catheterization and Cardiovascular Diagnosis*, 31:17-84 (1994).

Moussa, MD, Issaam "Stents Don't Require Systemic Anticoagulation . . . But the Technique (and Results) Must be Optimal," *Journal of Invasive Cardiol.*, 8(E):3E-7E, (1996).

Nakanishi et al., "Catheter Intervention to Venous System Using Expandable Metallic Stents," *Rinsho Kyobu Geka*, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386-392 (1998).

Theron et al., "New Triple Coaxial Catheter System for Carotid Angioplasty with Cerebral Protection," *American Journal of Neuroradiology*, 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Waksman et al., "Distal Embolization is Common After Directional Atherectomy . . . ," *American Heart Journal*, 129(3):430-435 (1995).

Wholey, Mark H. et al., PTA and Stents in the Treatment of Extracranial Circulation, *The Journal of Invasive Cardiology*, 8(E):25E-30E (1996).

* cited by examiner

HYDRAULIC CONTROLLED RETRACTABLE TIP FILTER RETRIEVAL CATHETER

BACKGROUND OF THE INVENTION

1. Field of the Invention

The present invention pertains to catheters for retrieving a distal protection filter. More precisely, the present invention pertains to retrieval catheters having a tapered distal tip.

2. Description of the Related Art

Heart disease is a major problem in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

During angioplasty and atherectomy procedures, embolic debris can be separated from the wall of the blood vessel. If this debris enters the circulatory system, it could block other vascular regions including the neural and pulmonary vasculature, both of which are highly undesirable. During angioplasty procedures, stenotic debris may also break loose due to manipulation of the blood vessel. Because of this debris, a number of devices, termed distal protection devices, have been developed to filter out this debris.

BRIEF SUMMARY OF THE INVENTION

The present invention pertains to distal protection filter retrieval catheters. The retrieval catheter may include an inner tube, an outer tube disposed over the inner tube, a lumen disposed between the inner tube and the outer tube, and a tapered member coupled to the lumen. The tapered member may include, for example, a distal tip or a rolling membrane movable between a first position and a second position.

The first position may comprise the most appropriate position for advancing the catheter across, for example, a stent or lesion. The second position may comprise the most appropriate position for retrieving a distal protection filter. Shifting the tapered member between the first position and the second position may occur by, for example, altering fluid pressure, venting fluid, or infusing fluid into the lumen.

DETAILED DESCRIPTION OF THE INVENTION

Figure 1:
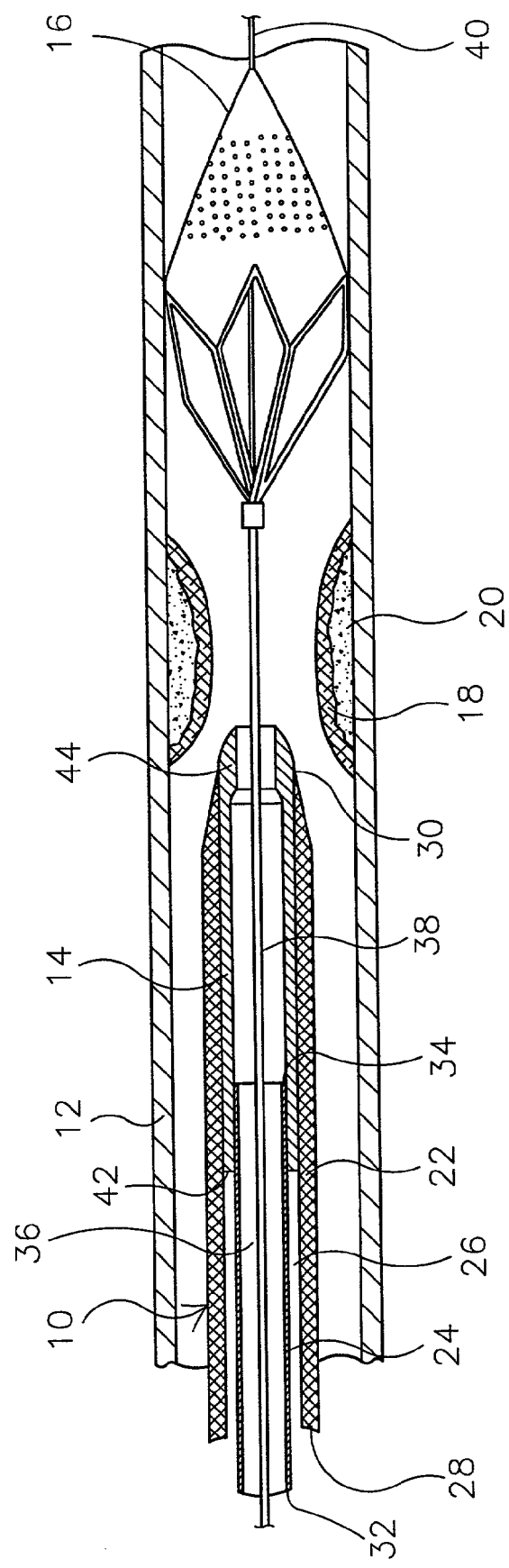
FIG. 1 is a cross-section of a distal protection filter retrieval catheter disposed within a blood vessel including a tapered member in a first position.

The following description should be read with reference to the drawings wherein like reference numerals indicate like elements throughout the several views. The detailed description and drawings illustrate example embodiments of the claimed invention.

FIG. 1 is a cross-section of a distal protection filter retrieval catheter 10 disposed within a blood vessel 12 and including a tapered member 14 configured in a first position. Removing a distal protection filter 16 from blood vessel 12 following an intravascular procedure may be complicated by a number of factors. For example, if the intravascular procedure includes the placement of a stent 18 adjacent a lesion 20, a retrieval catheter may catch or otherwise engage stent 18, which could lead to the displacement of stent 18. To minimize the chance of disrupting stent 18 or any other interventions that may be present adjacent lesion 20, distal protection filter retrieval catheter 10 has been designed to include a tapered member 14 that may assist passing catheter 10 past lesion 20 while causing minimal disruption of stent 18.

Catheter 10 includes an outer tube 22 disposed over an inner tube 24 and including an annular lumen 26 disposed therebetween. Outer tube 22 includes a proximal end 28 and a distal end 30. Outer tube 22 may be comprised of a polymer, stainless steel or nickel-titanium alloy hypodermic tubing, or a composite thereof. Alternatively, outer tube 22 may be generally comprised of metals, polymers, or composites thereof.

Inner tube 24 includes a proximal end 32, a distal end 34, and an inner lumen 36 extending therethrough. Similar to what is stated above for outer tube 22, inner tube 24 may be comprised of metals, polymers, or composites thereof. Inner lumen 36 may comprise a guidewire lumen adapted and configured to have a guidewire, core wire, etc. disposed therein.

Tapered member 14 may include a proximal end 42 and a tapered distal tip 44. Tapered member 14 may be coupled to lumen 26. For example, tapered member may comprise a polymeric, metallic, or composite tubular member slidably disposed within lumen 26. In addition, the position of tapered member may be maintained or otherwise altered by altering the pressure and/or the amount of fluid within lumen 26.

Tapered member 14 is movable between a first position and a second position. According to this embodiment, the first position is understood to be tapered member 14 configured such that at least a portion of distal tip 44 thereof extends beyond distal end 30 of outer tube 22. The first position may be the most appropriate position for tapered member 14 when advancing catheter 10 across stent 18 or lesion 20 toward filter 16.

Distal protection filter 16 may be coupled to a generally metallic elongate shaft 38, for example proximate a distal end 40 thereof. When using catheter 10 to retrieve filter 16 from blood vessel 12, catheter 10 may pass over shaft 38 to a location proximate filter 16. According to this embodiment, at least a portion shaft 38 may extend through inner lumen 36.

Filter 16 and shaft 38 may generally comprise a number of configurations known to those skilled in the appropriate art. Filter 16 may be comprised of a polyurethane sheet and include at least one opening that may be, for example, formed by known laser techniques. The holes or openings are sized to allow blood flow therethrough but restrict flow of debris or emboli floating in the body lumen or cavity.

Filter 16 may be generally cone-shaped, and have a proximal and a distal end. The distal end may be a narrow, "V"-shaped end and can be fixedly secured or formed to shaft 38. The proximal end has a relatively wide opening. Alternatively, filter 16 may be cylindrical with a relatively rounded distal end.

Filter 16 operates between a closed collapsed profile and an open radially-expanded deployed profile for collecting debris in a body lumen. Filter 16 may include a collapsible proximally-tapered frame having a mouth and a plurality of longitudinally-extending ribs. In an expanded profile, the mouth is opened and the ribs extend radially outwardly to support the mouth. In an alternate embodiment, filter 16 may comprise a number of differing objects including, but not limited to, a filter, a basket, a filter basket, a sheath, a capture sheath, a capturing device, one or more struts, one or more ribs, a mesh, a net, an expandable object, a self-expanding object, and combinations thereof. A number of differing configurations of filter 16 may be substituted without departing from the spirit of the invention.

Figure 2:
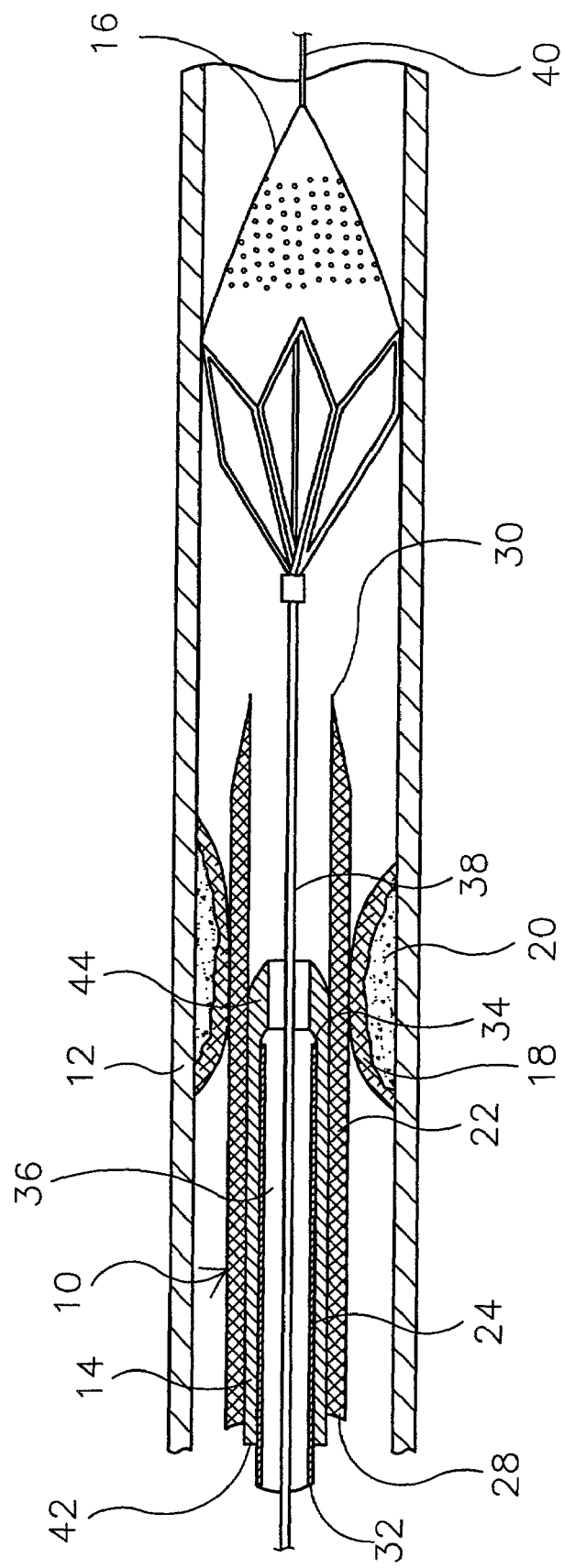
FIG. 2 is a cross-section of the distal protection filter retrieval catheter of FIG. 1 having the tapered member in a second position.

FIG. 2 is a cross-section of distal protection filter retrieval catheter 10 having tapered member 14 in a second position. The second position is understood to be tapered member 14 configured so that distal tip 44 may be disposed proximal to distal end 30 of outer tube 22. The second position may be the most appropriate position for retrieving filter 16. Accordingly, when tapered member 14 is in the second position, the inside diameter of tapered member may be sufficiently sized to accommodate filter 16 and allow removal thereof from blood vessel 12.

Inner tube 24 and outer tube 22 may be configured such that distal end 30 of outer tube 22 extends distally beyond distal end 34 of inner tube 24. The length that outer tube 22 extending distally of inner tube may be sized appropriated for having filter 16 disposed therein. Shifting tapered member 14 from the first position to the second position would shift the inside diameter of catheter 10 from that of tapered member 14 or inner tube 24 to that of the inside diameter of outer tube 22. Increasing the inside diameter of catheter 10 makes it possible for filter 16 to be disposed therein, either collapsed or partially collapsed.

To shift tapered member 14 between the first and the second positions, a clinician alters the fluid pressure or vent fluid from lumen 26. For example, a quantity of fluid may be disposed within lumen 26 that exerts a force upon tapered member 14 so as to hold it in the first position. With tapered member 14 in the first position, catheter 10 may be advanced across stent 18 or lesion 20. Once catheter is positioned across stent 18, the fluid can be vented from lumen 26. Venting fluid from lumen 26 will essentially remove the force exerted by the fluid on tapered member 14 and allow it to shift to the second position. The actual shift may occur by a number of mechanisms. For example, once catheter 10 encounters filter 16, proximal movement of filter 16 into catheter 10 may exert a force on tapered member 14 in the proximal direction and, thus, shift it into the second position.

Alternatively, tapered member 14 may be biased to be in the second position (e.g., by a spring, etc.). According to this embodiment, force exerted upon tapered member 14 by the fluid may be acting to overcome the bias and hold tapered member 14 in the first position. Venting the fluid would allow the bias in position of tapered member 14 to shift tapered member 14 to the second position.

Figure 3:
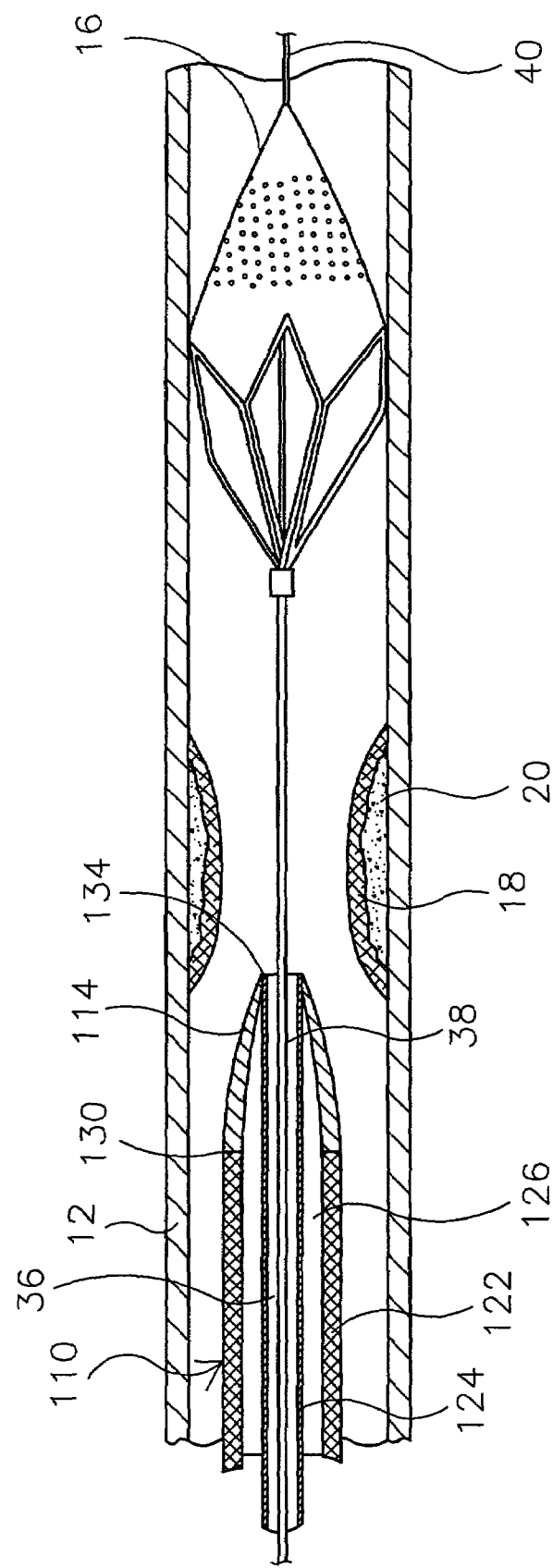
FIG. 3 is a cross-section of an alternate distal protection filter retrieval catheter disposed having a tapered member in a first position.

FIG. 3 is a cross-section of an alternate distal protection filter retrieval catheter 110 having a tapered member 114 in a first position. Catheter 110 is essentially the same in form and function as catheter 10 except that tapered member 114 comprises a rolling membrane and that inner tube 124 and outer tube 122 are configured such that distal end 134 of inner tube 124 extends distally beyond distal end 130 of outer tube 122.

Tapered member 114 may be comprised of a polymer or combination of polymers extending between distal end 130 of outer tube 122 and distal end 134 of inner tube 124 and be generally tapered and having a relatively low profile. Tapered member 114 is in fluid communication with lumen 126. Similar to what is described above, lumen 126 may include a fluid or other means for exerting force onto tapered member 114. In alternate embodiments, tapered member 114 may be relatively inelastic or be elastic.

Similar to what is described above, tapered member 114 may be shifted between the first and the second positions by, for example, altering the fluid pressure, infusing fluid, or venting fluid from lumen 126. The first position of tapered member 114 is understood to be where at least a portion of tapered member 114 is disposed proximal to distal end 134 of inner tube 124. With tapered member 114 in the first position, catheter 110 may be advanced across stent 18 or lesion 20. Once catheter 110 is positioned across stent 18, the fluid can be infused into lumen 126. Infusing fluid into lumen 126 will exert a force on tapered member 114 and cause it to move or roll distally, and shift it to the second position.

Figure 4:
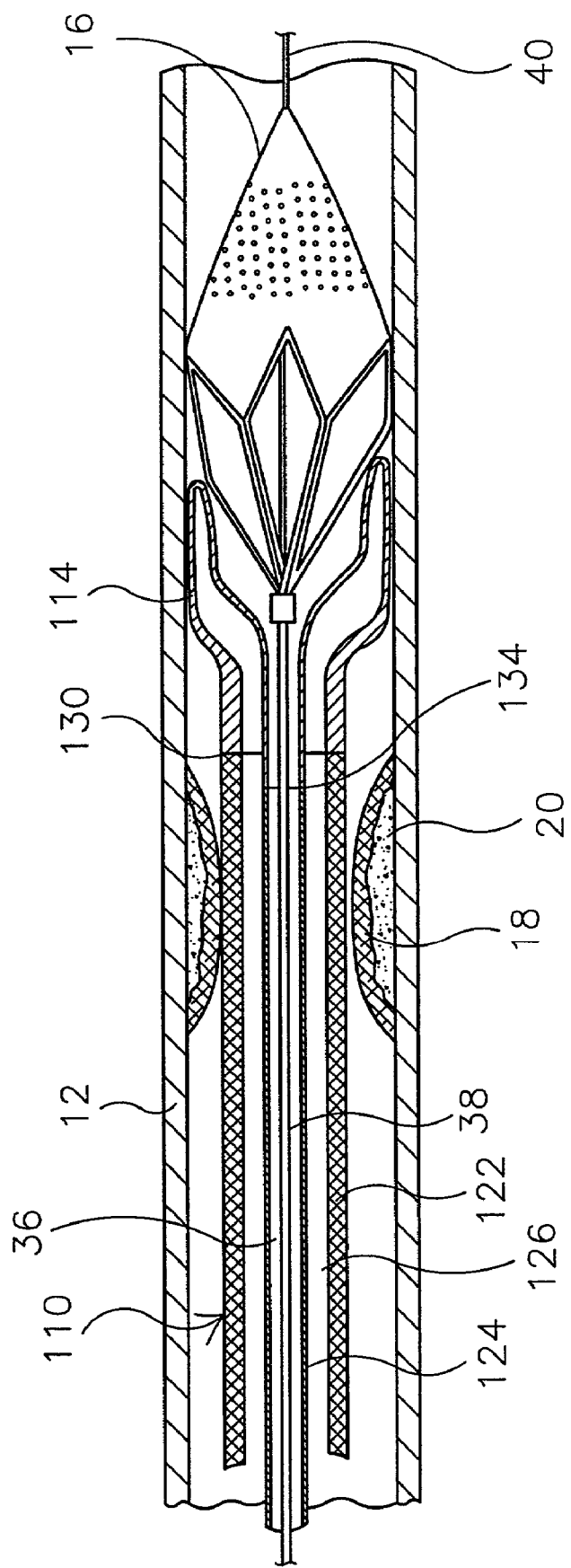
FIG. 4 is a cross-section of the distal protection filter retrieval catheter of FIG. 3 having a tapered member in a second position.

FIG. 4 is a cross-section of distal protection filter retrieval catheter 110 having tapered member 114 in a second position. The second position is understood to be a configuration of tapered member 114 wherein at least a portion thereof extends distally of distal end 134 of inner tube 124. When tapered member 114 shifts from the first position to the second position, outer tube 122 may move distally relative to inner tube 124. This movement may be due to force exerted by the fluid onto tapered member 114 being transferred to outer tube 122. Alternatively, the position of outer tube 122 may be fixed relative to inner tube 124.

It can be appreciated that the first position of tapered member 114 would be the appropriate position for advancing tapered member 114 past lesion 20 or stent 18, and the second position is the position that would be appropriate for retrieving filter 16. According to this embodiment, the second position would configure catheter 110 with an inside diameter (e.g., the inside diameter defined by tapered member 114 or outer tube 122) that is sized for having filter 16 disposed therein.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A filter retrieval catheter, comprising:
   an inner tube having a proximal end, a distal end, and an inner lumen extending therethrough;

an outer tube disposed over the inner tube, the outer tube including a proximal end and a distal end; wherein an annular lumen is defined between the inner tube and the outer tube;

a filter disposed on a shaft, the shaft disposed at least in part in the inner lumen proximate the distal end of a sheath; and a tip member including a rolling member in fluid communication with the annular lumen, the rolling member adapted and configured to transition between a first tapered position for advancing to the filter and a second expanded position for receiving the filter, the rolling member configured to transition by a change in fluidic pressure within the annular lumen.

2. The filter retrieval catheter in accordance with claim 1, wherein, in the first position at least a portion of the rolling member is disposed proximal to the distal end of the inner tube.

3. The filter retrieval catheter in accordance with claim 1, wherein, in the second position at least a portion of the rolling membrane extends distally of the distal end of the inner tube.

* * * * *

UNITED STATES PATENT AND TRADEMARK OFFICE
CERTIFICATE OF CORRECTION

| | |
|---|---|
| PATENT NO. | : 7,153,320 B2 |
| APPLICATION NO. | : 10/017877 |
| DATED | : December 26, 2006 |
| INVENTOR(S) | : Charles L. Euteneuer et al. |

It is certified that error appears in the above-identified patent and that said Letters Patent is hereby corrected as shown below:

Column 5
Line 6 and 7, delete "proximate the distal end of a sheath".

Signed and Sealed this

Twenty-fourth Day of April, 2007

JON W. DUDAS
*Director of the United States Patent and Trademark Office*